United States Patent [19]

Snijder et al.

[11] Patent Number: 5,710,306

[45] Date of Patent: Jan. 20, 1998

[54] PROCESS TO PREPARE A MULTIDENTATE PHOSPHITE COMPOUND

[75] Inventors: Carina S. Snijder, Sittard; Antonius J. J. M. Teunissen, Geleen; Carolina B. Hansen, Sittard, all of Netherlands; Rafael Shapiro; James M. Garner, both of Wilmington, Del.

[73] Assignees: DSM N.V., Heerlen, Netherlands; E. I. Du Pont de Nemours and Company, Wilmington, Del.

[21] Appl. No.: 616,747

[22] Filed: Mar. 15, 1996

[51] Int. Cl.$^6$ ............................................. C07F 9/145
[52] U.S. Cl. ................................................. 558/93
[58] Field of Search ................................................. 558/93

[56] References Cited

U.S. PATENT DOCUMENTS

| 4,668,651 | 5/1987 | Billig et al. | 502/158 |
| 5,235,113 | 8/1993 | Sato et al. | 568/454 |

FOREIGN PATENT DOCUMENTS

95/18089  7/1995  WIPO .

OTHER PUBLICATIONS

Perich, John W. and R.B. Johns; Synthesis Feb. 1988: (2), 142–144.

*Primary Examiner*—Michael G. Ambrose
*Attorney, Agent, or Firm*—Cushman Darby & Cushman IP Group of Pillsbury Madison & Sutro, LLP

[57] ABSTRACT

A process to prepare a multidentate phosphite compound according to the general formula (1)

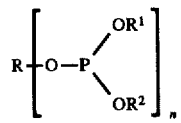

in which n is 2–6, R is an n-valent organic group and $R^1$ and $R^2$ are fused aromatic ring systems with 2 or more rings, which rings are substituted on the ortho position relative to the oxygen atom only with hydrogen, by first preparing a phosphorochloridite compound from a $R^1$—OH and $R^2$—OH alcohol compound and a phosphorus chloride compound and subsequently contacting the phosphorochloridite compound with an alcoholic compound according to R—(OH)$_n$, wherein the phosphorochloridite is prepared by performing the two steps in a solvent:

a) contacting a compound with the general formula:

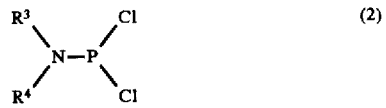

(2)

in which $R^3$ and $R^4$ are $C_1$–$C_4$ alkyl groups, with the $R^1$OH and $R^2$OH compounds, and b) contacting the resulting compound of step (a) which has the formula (3):

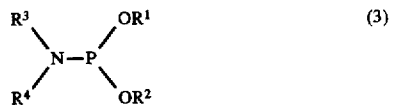

(3)

with HY, wherein Y is a halogen.

16 Claims, No Drawings

5,710,306

1

PROCESS TO PREPARE A MULTIDENTATE PHOSPHITE COMPOUND

FIELD OF THE INVENTION

The invention relates to a process to prepare a multidentate phosphite compound represented by the general formula (1)

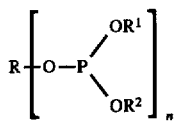

in which n is 2–6, R is an n-valent organic group and $R^1$ and $R^2$ are fused aromatic ring systems having 2 or more rings. The rings of $R^1$ and $R^2$ are substituted in the ortho position (relative to the oxygen atom), only with hydrogen, provided that substitution is possible. The phosphite compounds are prepared by first preparing a phosphorochloridite compound starting from $R^1$—OH and $R^2$—OH alcohol compounds and a phosphorous chloride compound. In a subsequent step, the phosphorochloridite compound is contacted with an alcoholic compound $R$—$(OH)_n$ to yield the phosphite.

BACKGROUND OF THE INVENTION

U.S. Pat. No. 5,235,113 discloses the preparation of a phosphorochloridite by reacting 3,6-di-tert-butyl-2-naphthol dissolved in triethylamine and $PCl_3$ dissolved in toluene. A bidentate phosphite is subsequently prepared by contacting the phosphorochloridite compound with 2,2'-biphenyldiol in triethylamine.

Disadvantages of this known process include the difficulty in preparing the intermediate phosphorochloridite compound in a high yield when starting from alcohols ($R^1OH$ and $R^2OH$) in which the steric bulk around the hydroxyl group is not sufficiently large. In this case, the main product will be a triorganophosphite compound in which the organogroups correspond to the starting alcohol compound. The formation of this compound can be explained by the relatively minimal steric hinderance around the P—O bond of the phosphite, which makes it possible for three moles of alcohol to react with one mole of $PCl_3$.

There is a need for a process in which these phosphorochloridite compounds can be prepared in a high yield. The phosphorochloridite compounds are needed to prepare the class of multidentate phosphite compounds represented by formula (1) which presently are difficult to obtain.

SUMMARY AND OBJECTS OF THE INVENTION

This need is satisfied by the present process in which the phosphorochloridite compound is prepared by performing the following two steps in a solvent:

a) contacting a compound represented by the general formula:

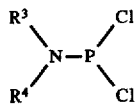

in which $R^3$ and $R^4$ are $C_1$–$C_4$ alkyl groups, with the $R^1OH$ and $R^2OH$ compounds, and b) contacting the resulting compound of step (a) which is represented by the formula (3):

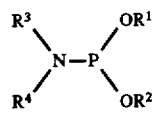

with HY, wherein Y represents a halogen atom.

The present invention makes it possible to prepare the phosphorochloridite compound and thus the phosphite compound represented by formula (1) in a high yield.

A method for preparing phosphite compounds directly, in one step, from a dialkyl-N,N'-dialkylphosphoramide compound and a mono-alcohol is described in Synthesis, 1988, 2, 142. The resulting phosphite compound is, however, a monodentate phosphite compound. It appeared difficult to prepare a multidentate phosphite compound directly in an analogous method by starting from a compound, $R(OH)_n$, with more than one alcohol functionality (n>1).

DETAILED DESCRIPTION OF THE INVENTION

Starting alcoholic compounds $R^1OH$ and $R^2OH$ preferably have 10–30 carbon atoms and preferably comprise 2 to 4 fused aromatic rings. Examples are naphthol, anthranol and phenanthrol. All carbon atoms adjacent or ortho to the hydroxyl group substituted carbon atom are substituted, if possible, only with hydrogen. Other carbon atoms of the fused rings may optionally be substituted with other groups, for example alkoxy, alkyl, amine and halogen groups. Preferably, $R^1$ and $R^2$ are the same group. $R^1$ and $R^2$ are preferably 9-phenanthryl or 1-naphthyl groups.

Step (a) can be performed in substantially the same manner as described in Synthesis, 1988, 2, 142–144, the complete disclosure of which is incorporated herein by reference. This article describes the preparation of alkyl and aryl di-tert-butyl phosphates using di-tert-butyl N,N-diethylphosphoramidite as an intermediate compound. This intermediate compound is analogous to the compound represented by formula (3).

The compound according to formula (2) can be obtained by methods known to those skilled in the art. For example, methods can be used substantially analogous to those described in Synthesis, 1988, 2, 142–144.

$R^3$ and $R^4$ are, independent of one another, $C_1$–$C_4$ alkyl, such as for example methyl, ethyl, propyl, butyl or tert-butyl. Preferably, $R^3$ and $R^4$ the same group.

In Step (a), the compound according to formula (2) is contacted in a suitable solvent with the $R^1OH$ and $R^2OH$, preferably in the presence of a base. Examples of bases include organic bases such as, for example, a trialkylamine having 2 to 12 carbon atoms. Examples of suitable solvents include ethers like, for example, diethyl ether, dioxane or tetrahydrofuran and aromatic solvents like, for example, benzene or toluene. Step (a) is preferably performed at a temperature between about −80° and about 60° C., and more preferably, at about room temperature.

The concentration of the compound represented by formula (2) is preferably between about 0.01 and about 5 mol/l. The molar ratio of $R^1OH$ and $R^2OH$ and the compound (2) is preferably stoichiometric. Other ratios may be possible, but generally, a greater effort is then needed to purify the product.

In Step (b), the Y of HY can be F, Cl, Br or I. A preferred HY is HCl. HY can be present in a gaseous form or dissolved in solvent such as, for example an ether like diethyl ether, dioxane or tetrahydrofuran or in an aromatic solvent like benzene or toluene. The temperature in step (b) is preferably between −80° and 60° C. The molar ratio of HY and compound (3) is preferably between about 0.8 and about 5.

The step (b) phosphorochloridite reaction product, e.g. a compound according to the general formula (3), is generally dissolved in a reaction mixture having precipitated $R^3R^4NH.HCl$ salt present. It can be advantageous to separate the salt from the phosphorochloridite compound before using this compound further. Separation is especially preferred when the $R-(OH)_n$ compound is not very reactive. Separation can be performed by, for example, filtration of the reaction mixture.

The phosphorochloridite compound thus obtained is subsequently contacted with an alcoholic compound according to $R-(OH)_n$ in which R is the n-valent organic group of formula (1) and n is 2 to 6.

The conditions for such a contacting in order to prepare the phosphite compound are generally known and are, for example, described in the aforementioned U.S. Pat. No. 5,235,113, the complete disclosure of which is hereby incorporated by reference. In general, the contacting is performed in a suitable solvent like, for example, the solvents for step (a). Preferably, contacting is performed in the presence of a base like, for example, an organic base like, for example, an alkylamine exemplified by triethylamine. The temperature is preferably between about −80° about 100° C.

The n-valent group R can be any of the organic bridging groups which are commonly known for multidentate phosphite compounds such as, for example those groups described in U.S. Pat. No. 5,235,113, EP-A-214622 and WO-A-9518089, the complete disclosures of which are incorporated herein by reference.

Preferably the n-valent group has at least two carbon atoms and less than 40 carbon atoms. The n-valent group can be, for example, alkylene groups or divalent aromatic groups. Examples of suitable alkylene groups include ethylene, trimethylene, tetramethylene or pentamethylene. Examples of alcohols according to $R-(OH)_n$, which are the building blocks of the n-valent organic group, include 2,5-di-t-butylhydroquinone, 2,5-di-t-amylhydroquinone, 2,5-dimethylhydroquinone, 4,6-di-t-butylresorcinol, 4,4'-isopropylidenebisphenol, 4,4'-methylenebis(2-methyl-6-t-butylphenol), 4,4'-oxobis(2-methyl-6-isopropylphenol), 4,6'-butylidenebis (3-methyl-6-t-butylphenol), 2,2'-biphenyldiol, 3,3',5,5'-tetramethyl-2,2'biphenyldiol, 3,3',5,5'-tetra-t-butyl-2,2'-biphenyldiol, 3,3'-dimethoxy-5,5'-dimethyl-2,2'-biphenyldiol, 3,3'-di-t-butyl-5,5'-dimethoxy-2,2'-biphenyldiol, 3,3'-di-t-butyl-5,5'-dimethyl-2,2'-biphenyldiol, 2,2'-methylenebis(4-methyl-6-t-butylphenol), 2,2'-methylenebis(4-ethyl-6-t-butylphenol), 2,2'-thiobis(4-methyl-6-t-butylphenol), 2,2'-thiobis(4-t-butyl-6-methylphenol), 2,2'-thiobis(4,6-di-t-butylphenol), 1,1'-thiobis(2-naphthol), catechol, 2,3-dihydroxynapthalene, 1,8-dihydroxynaphthalene, 1,4-dihydroxynaphthalene, 1,3,5-trihydroxybenzene, 1,1'-methylenebis(2-naphthol), 1,1'-di-2-naphthol, 10,10'-di-9-phenanthrol, ethyleneglycol, 1,3-propanediol, 1,2-butanediol, 1,4-butanediol, pentaerythritol, trans-1,2-cyclohexanediol, cis-1,2-cyclohexanediol, cis-1,2-cyclohexanedimethanol, cis-1,2-cyclododecanediol, and the like.

A preferred and novel class of bidentate phosphite compounds represented by formula (1) have a group R according to the following formula (4):

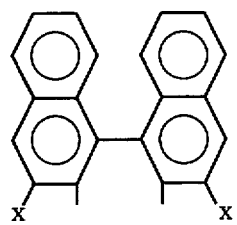

(4)

in which X is hydrogen or an organic group. Preferably, both X substituents are an organic group, and more preferably, an alkyl group, an aryl group, a triarylsilyl group, a trialkylsilyl group, a carboalkoxy group, a carboaryloxy group, an aryloxy group, an alkoxy group, an alkylcarbonyl group, an arylcarbonyl group, an amide or a nitrile group. The present invention is also directed to this novel bidentate phosphite ligand.

The alkyl group is preferably a $C_1$–$C_{10}$ alkyl group such as, for example methyl, ethyl, propyl, isopropyl, butyl, tert-butyl, isobutyl, pentyl or hexyl. Exemplary of a triarylsilyl group is triphenylsilyl and examples of a trialkylsilyl group are trimethylsilyl and triethylsilyl. Preferred aryl groups have 6 to 20 carbon atoms, such as, for example, benzyl, tolyl, naphthyl or phenanthryl. Preferred aryloxy groups have 6 to 12 carbon atoms and include, for example phenoxy. Preferred alkoxy groups have 1 to 10 carbon atoms and include, for example, methoxy, ethoxy, tert-butoxy or isopropoxy. Preferred alkylcarbonyl groups have 2 to 12 carbon atoms and include, for example, methylcarbonyl and tert-butylcarbonyl. Preferred arylcarbonyl groups have 7 to 13 carbon atoms such as, for example, phenylcarbonyl.

X is most preferably a carboalkoxyl or carboaryloxy group, $-CO-O-R^3$, in which $R^3$ is an alkyl group having 1 to 20 carbon atoms or an aryl group having 6–12 carbon atoms. Examples of suitable R groups include methyl, ethyl, propyl, isopropyl, n-butyl, tert-butyl, isobutyl, phenyl, tolyl. Even more preferably, both X substituents are the same carboalkoxyl group.

The phosphite compounds having a bridging group R represented by formula (4) as described above can be advantageously used as part of a homogeneous catalyst system also comprising rhodium. Such a catalyst system is preferably used for the hydroformylation reaction of an unsaturated organic compound, and especially, of an internally unsaturated organic compound to a terminal aldehyde organic compound. High reaction rates and high selectivities to linear or terminal aldehyde products can be achieved when using such catalyst system.

It has been found, for example, that when using such a catalyst system, the reaction of a $C_1$–$C_6$ alkyl 3-pentenoate ester to the $C_1$–$C_6$ alkyl 5-formylvalerate ester proceeds with a high selectivity, yield and reaction rate when compared to state of the art processes, such as, for example, processes described in WO-A-9518089, the complete disclosure of which is hereby incorporated by reference. The present invention is also directed to a process for preparing $C_1$–$C_6$ alkyl 5-formylvalerate esters. Preferably, the alkyl is methyl or ethyl.

Preferably, the multidentate phosphite compound represented by formula (1) as obtained by the process of the invention is used as a polymer stabilizer. Preferably, the multidentate phosphite compound represented by formula (1) as obtained by the process of the invention is used as a fire retarding additive or filler.

Preferably, the multidentate phosphite compound as obtained by the process of the invention is used as part of a homogeneous catalyst system also comprising a metal of Group VIII. The homogeneous catalyst system can be used for the isomerization of olefins. More preferably, the homogeneous catalyst system is used in the hydroformylation of an ethylenically unsaturated organic compound to a terminal aldehyde compound. Preferably the unsaturated compound is a pentenoic acid, or its corresponding ester or nitrile, and the Group VIII metal is rhodium. The resulting 5-formylvaleric acid, or its corresponding ester or nitrile, are important intermediates in a process to prepare precursors for Nylon-6 and Nylon-6,6.

The invention will be elucidated with the following non-limiting examples.

EXAMPLE I 3.88 g (20 mmol) 9-phenanthrol was dissolved in 250 ml toluene and water was removed by azeotropic distillation. Subsequently, 2.3 g triethylamine and 1.74 g (10 mmol) diethylaminophosphorous dichloride were added at room temperature while stirring. In this way, diethylamino diphenanthrene phosphite was synthesized ($^{31}$P NMR δ 138.7 ppm). To obtain diphenanthrene phosphorous chloride, 22 ml of a 1 M HCl solution in diethyl ether was added ($^{31}$P NMR δ 161.4 ppm). The reaction mixture was filtered, and to the filtrate, 3 g (30 mmol) of triethyl amine and 1.98 g of dimethyl 2,2'-dihydroxy-1,1'-binaphthalene-3,3'-dicarboxylate were added. After stirring for 10 minutes, the reaction was completed and NEt$_3$.HCl was removed by filtration (Et=ethyl). The solvent was removed and the product was purified by crystallization from acetonitrile/toluene ($^{31}$P NMR δ 126.6 ppm). The yield of product Compound 1, represented below, was 90%.

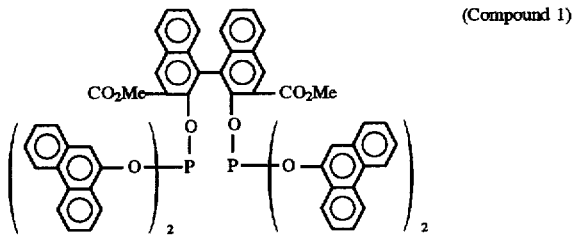

(Compound 1)

Comparative Example A

Compound 1 was also intended to be prepared starting from 9-phenanthrol by the synthetic route described in Example 10 of U.S. Pat. No. 5,235,113. It was, however, not possible to obtain the phosphorochloridite intermediate in a high yield (about 5%). Rather, tri(9-phenanthryl)phosphite was mainly obtained. The desired product in yield of only 5% could not be isolated easily. This experiment illustrates that it is difficult to prepare the Compound 1 by the prior art synthetic route as for example described in EP-A- 518241.

EXAMPLE II

A 150 ml Hastelloy-C steel autoclave (Parr) was filled under nitrogen with 5.8 mg Rh(acac)(CO)$_2$ (acac=acetylacetonate) (4.8×10$^{-5}$ mol), 14.0×10$^{-5}$ mol of Compound 1 as ligand (ligand/rhodium ratio (L/Rh)=2.9 mol/mol) and 60 ml of toluene. Hereafter, the autoclave was closed and purched with nitrogen. Next, the autoclave was brought to a pressure of 1 MPa using carbon monoxide/hydrogen (1:1) and heated to 90° C. in approx. 30 min. Subsequently, a mixture of 7.44 g (65 mmol) freshly distilled methyl 3-pentenoate and 1.2 gram of nonane topped up to 15 ml with toluene was injected into the autoclave. The composition of the reaction mixture was determined by gas chromatography. After 7 hours of reaction, a 90.1% conversion was determined. The selectivity to methyl 5-formylvalerate was 75.1%. The molar ratio of methyl 5-formylvalerate and the sum of methyl 3- and methyl 4-formylvalerate (n/b ratio) was 9.3, and the hydrogenation to methyl valerate was 5.7%.

EXAMPLE III

Example II was repeated in which the L/Rh ratio was 3.1 with a ligand represented by:

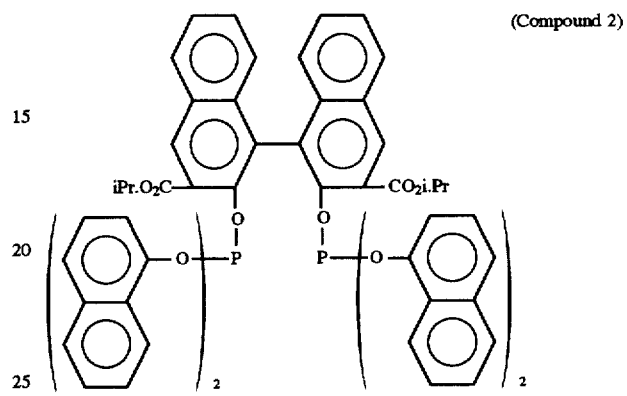

(Compound 2)

The conversion was 81.8% and the selectivity to methyl 5-formylvalerate was 84.6%.

EXAMPLE IV

Example I was repeated using as R—(OH). compound di-isopropyl 2,2'dihydroxy-1,1'-binaphthalene-3,3'-dicarboxylate and as R$^1$(OH) starting compound 9-phenanthrol. A compound represented by:

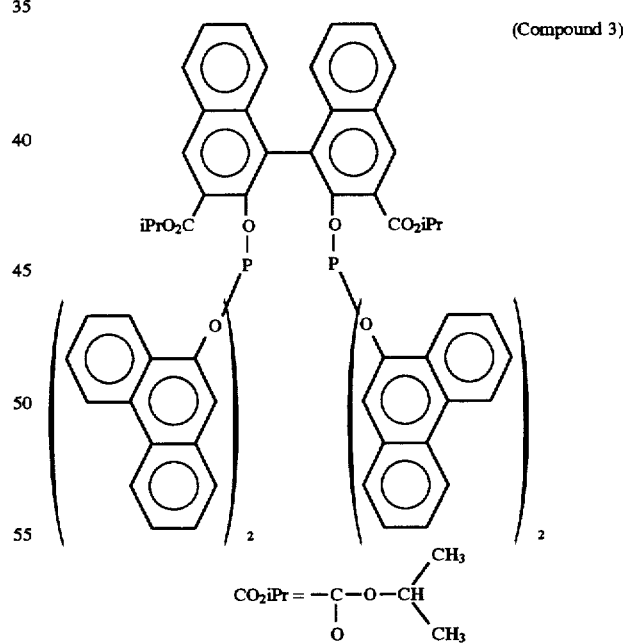

(Compound 3)

was obtained as a slightly yellow coloured powder in 85% yield.

EXAMPLE V

Example I was repeated using as R—(OH)$_n$ compound pentaerythritol and as R$^1$(OH) starting compound 1-naphthol. A compound represented by:

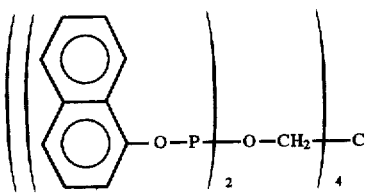

(Compound 4)

was obtained as a yellow coloured oil in a 80% yield.

EXAMPLE VI

Example I was repeated using as R—(OH)$_n$ compound diethyl 2,2'-dihydroxy-1,1'-binaphthalene-3,3'-dicarboxylate and as R$^1$(OH) starting compound 4-chloro-1-naphthol. The yield was about 90%.

While the invention has been described in detail and with reference to specific embodiments thereof, it will be apparent to those of ordinary skill in the art that various changes and modifications can be made therein without departing from the spirit and scope thereof.

What is claimed is:

1. A process for preparing a multidentate phosphite compound represented by the general formula (1)

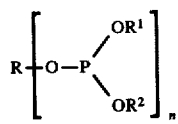

in which n is 2–6, R is an n-valent organic group and R$^1$ and R$^2$ are fused aromatic ring systems with 2 or more rings, which rings are substituted on the ortho position relative to the oxygen atom only with hydrogen, by first preparing a phosphorochloridite compound from a R$^1$—OH and R$^2$—OH alcohol compound and a phosphorus chloride compound and subsequently contacting the phosphorochloridite compound with an alcoholic compound according to R—(OH)$_n$, wherein the phosphorochloridite is prepared by performing the two steps in a solvent:

a) contacting a compound with the general formula:

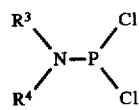

in which R$^3$ and R$^4$ are C$_1$–C$_4$ alkyl groups, with the R$^1$OH and R$^2$OH compounds, and b) contacting the resulting compound of step (a) which has the formula (3):

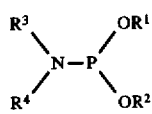

with HY, wherein Y represents F, Cl, Br or I.

2. A process according to claim 1, wherein R$^3$ and R$^4$ are the same alkyl group.

3. A process according to claim 1, wherein said HY is HCl and said HCl is dissolved in a solvent when contacting with the compound represented by formula (3).

4. A process according to claim 1, wherein HY is contacted with the compound represented by formula (3) in the solvent, and HY is gaseous HCl.

5. A process according to claim 1, wherein the temperature of step (a) and (b) is between about −80° and about 60° C.

6. A process according to claim 1, wherein the phosphorochloridite compound is separated from precipitated R$^3$R$^4$NH.HCl salt which forms as the phosphorochloridite compound forms.

7. A process according to claim 1, wherein R$^1$—OH and R$^2$—OH are naphthol, anthranol or phenanthrol.

8. A process according to claim 1, wherein the group R has between 2 to 40 carbon atoms.

9. A process according to claim 1, wherein n is 2.

10. A process according to claim 1, wherein the phosphite compound is represented by the following:

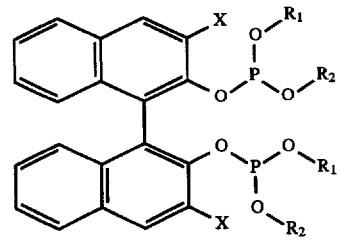

wherein X is hydrogen or an organic group and R$^1$ and R$_2$ are fused aromatic ring systems with 2 or more rings, which rings are substituted on the ortho position relative to the oxygen atom only with hydrogen.

11. A process according to claim 10, wherein X is a alkyl group, a aryl group, a triaryl silyl group, a trialkyl silyl group, a carboalkoxy group, a carboaryloxy group, an aryloxy group, an alkoxy group, an alkylcarbonyl group, an arylcarbonyl group, a nitrile group or an amide group.

12. A process according to claim 11, wherein X carboalkoxy group or a carboaryloxy group according to —Co—O—R$^3$, wherein R$^3$ is an alkyl group having one to 20 carbon atoms or an aryl group having 6–12 carbon atoms.

13. A process according to claim 10, wherein R$^1$ and R$^2$ are 1-naphthyl or 9-phenanthryl groups.

14. A process according to claim 10, wherein R$^3$ and R$^4$ are the same alkyl group.

15. A process according to claim 10, wherein said HY is HCl and said HCl is dissolved in a solvent when contacting with the phosphite compound.

16. A process according to claim 10, wherein said HY is gaseous HCl.

* * * * *